(12) United States Patent
Chu (10) Patent No.: US 11,040,145 B1
(45) Date of Patent: Jun. 22, 2021

(54) PLUNGER UNIT CREATING INTERMITTENT AUDIO SIGNALS AND A MEDICAMENT DELIVERY DEVICE HAVING THE UNIT

(71) Applicant: CAREBAY EUROPE LTD, Sliema (MT)

(72) Inventor: Chun Chu, Taipei (TW)

(73) Assignee: SHL MEDICAL AG, Zug (CH)

( * ) Notice: Subject to any disclaimer, the term of this patent is extended or adjusted under 35 U.S.C. 154(b) by 566 days.

(21) Appl. No.: 16/070,614

(22) PCT Filed: Dec. 22, 2016

(86) PCT No.: PCT/EP2016/082409
§ 371 (c)(1),
(2) Date: Jul. 17, 2018

(87) PCT Pub. No.: WO2017/129337
PCT Pub. Date: Aug. 3, 2017

(30) Foreign Application Priority Data

Jan. 26, 2016 (SE) .................................... 1650085-2

(51) Int. Cl.
*A61M 5/315* (2006.01)

(52) U.S. Cl.
CPC ... *A61M 5/31511* (2013.01); *A61M 2205/581* (2013.01); *A61M 2205/582* (2013.01)

(58) Field of Classification Search
CPC .... A61M 5/31511; A61M 5/315; A61M 5/20; A61M 2005/2013; A61M 2205/581; A61M 2205/582
See application file for complete search history.

(56) References Cited

U.S. PATENT DOCUMENTS

| 7,758,550 B2 | 7/2010 | Bollenbach et al. |
| 2008/0262438 A1 | 10/2008 | Bollenbach et al. |

FOREIGN PATENT DOCUMENTS

| TW | 201408344 A | 3/2014 |
| WO | 2011/123024 A1 | 10/2011 |

OTHER PUBLICATIONS

International Search Report and Written Opinion for Int. App. No. PCT/EP2016/082409, dated Mar. 31, 2017.

*Primary Examiner* — Deanna K Hall
(74) *Attorney, Agent, or Firm* — McDonnell Boehnen Hulbert & Berghoff LLP (57) ABSTRACT

A plunger unit is presented having rod member and a plunger body, movably mounted to the rod member, a striker movably mounted between the plunger body and the rod member, and a first biasing member urging the plunger body and the rod member, wherein the striker impacts the plunger body to create signals when the first biasing member activates a movement of the plunger body relative to the rod member. A medicament delivery device is also presented having a proximal sub-assembly and a distal sub-assembly movably connected to the proximal sub-assembly, where the plunger unit is received in the distal sub-assembly.

20 Claims, 9 Drawing Sheets

PLUNGER UNIT CREATING INTERMITTENT AUDIO SIGNALS AND A MEDICAMENT DELIVERY DEVICE HAVING THE UNIT

CROSS REFERENCE TO RELATED APPLICATIONS

The present application is a U.S. National Phase Application pursuant to 35 U.S.C. § 371 of International Application No. PCT/EP2016/082409 filed Dec. 22, 2016, which claims priority to Swedish Patent Application No. 1650085-2 filed Jan. 26, 2016. The entire disclosure contents of these applications are herewith incorporated by reference into the present application.

FIELD OF INVENTION

This invention generally relates to an automated medicament delivery device, and more particularly to such a device having a plunger unit which is able to create intermittent audio signals.

BACKGROUND

The patent application WO 2011-123024 discloses a related medicament delivery device, which may be incorporated into the present application for reference.

As to the intermittent auto signals, the U.S. Pat. No. 7,758,550 discloses a signaling unit. The conventional signaling unit 1, as shown FIG. 1, includes a catch rod 11 on which a plurality of unidirectional ratchet teeth 111 are formed and an engaging sleeve 12 whose end is bent inwards to form a flexible engaging portion 121. The catch rod 11 is received in the engaging sleeve 12.

Figure 1:
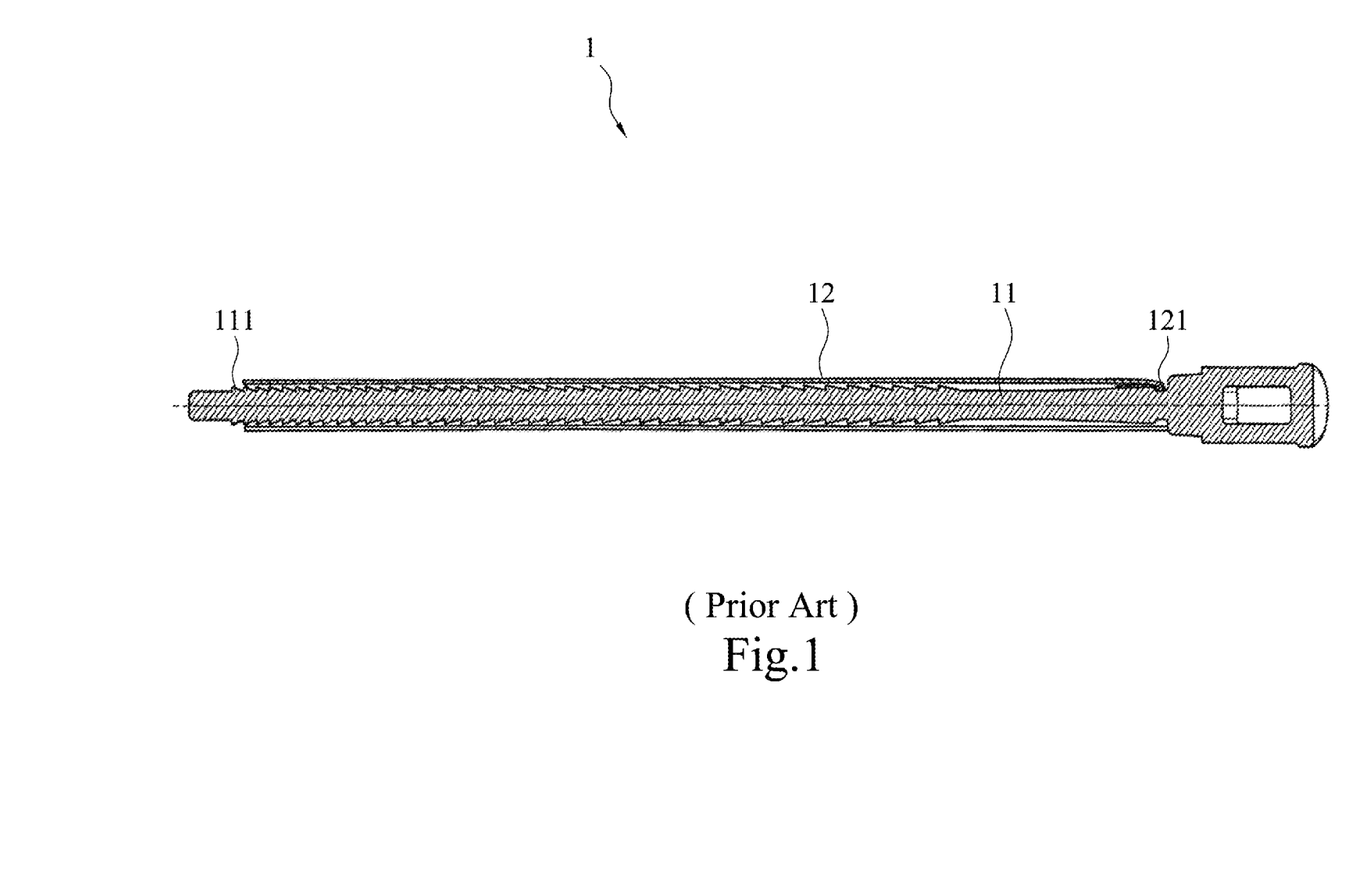
FIG. 1 is an assembled sectional view illustrating a conventional signaling unit of a medicament delivery device.

When the engaging sleeve 12 is moved relative to the catch rod 11, the flexible engaging portion 121 slides from one ratchet tooth 111 to next ratchet tooth 111 and strikes the next ratchet tooth 111 to create an acoustic signal for the user.

However, the catch rod 11 is difficult to mount in the engaging sleeve 12 because the ratchet teeth 111 of the catch rod 11 are unidirectional and the inner diameter of the engaging portion 121 of the engaging sleeve 12 is normally smaller than the outer diameter of the ratchet teeth 111. Therefore, the engaging portion 121 will be blocked by the ratchet teeth 111 when the catch rod 11 is inserted into the engaging sleeve 12 unless the flexible engaging portion 121 is temporarily bent outwards.

SUMMARY

Accordingly, this invention relates to a plunger unit and a medicament delivery device having the plunger unit, which is intended to obviate one or more of the problems arising from the limitations and disadvantages encountered in the prior art.

One object of this invention is to provide a medicament delivery device which can create intermittent audio signals and/or tactile feedback during injection.

Another object of this invention is to provide a medicament delivery device which is easy to assemble.

Yet another object of this invention is to provide a medicament delivery device which can inject a highly viscous content.

A further object of this invention is to provide a medicament delivery device which is compact.

These objects are achieved by a plunger unit as defined by claim 1 and a medicament delivery device as defined by claim 10. The dependent claims define preferred or advantageous embodiments of the plunger unit and the medicament delivery device.

Additional features and advantages of the present invention will be set forth in the description which follows, and in portion will be apparent from the description, or may be learned by practice of the present invention. The objectives and advantages of the present invention will be realized and attained by the structure as particularly set forth in the written description and claims as well as illustrated in the appended drawings.

To achieve these and other advantages and according to the purpose of this invention, as embodied and broadly described, a plunger unit comprises: a plunger body; a rod member movably mounted to the plunger body; and a first biasing member including two ends which respectively urges the plunger body and the rod member; and is characterized in that a striker is movably mounted between the plunger body and the rod member, wherein the striker impacts the plunger body or the rod member to create signals when the first biasing member activates a movement of the plunger body relative to the rod member.

It is preferred that the plunger unit further comprises a second biasing member urging the striker and the plunger body. The second biasing member may make the audio signals loud and/or tactile feedback clear.

Moreover, the plunger unit further comprises a blocker connected to the plunger body and the second biasing member urging the striker and the blocker.

Another preferred feature is that the striker and the second biasing member are movably received in the plunger body and the first biasing member is sleeved outside the plunger body. Since the first biasing member is arranged outside the plunger body rather than inside the plunger body, the recovery force of the first biasing member with larger dimensions is large enough to expel a highly viscous medicament from a container.

Additionally, the plunger body includes a plunger head. A plunger sleeve connected to the plunger head and a plug received in the plunger sleeve. The striker and the second biasing member are received in the plunger sleeve and the first biasing member is sleeved outside the plunger sleeve. The rod member passes through the second biasing member and the striker.

Furthermore, the rod member includes a rod body and a plurality of bumps on the rod body. The rod body passes through the second biasing member and the striker. The bumps interfere with the striker when the striker is moved along the rod body.

It is preferred that the striker is C-shaped and/or has a wedge-shaped rib to facilitate the striker sliding over a bump of the rod member.

It is preferred that the striker is in a ring and/or has a wedge-shaped rib to facilitate the striker sliding over a bump of the rod member.

It is preferred that the rod member further includes a rod head from which the rod body extends. The first biasing member urges the rod head and the plunger body.

It is preferred that the rod member includes a rod head, a rod body extending from the rod head, and a plurality of bumps on the rod body. The first biasing member urges the rod head and the plunger head.

Another aspect of this invention directs to a medicament delivery device comprising: a proximal sub-assembly; and a distal sub-assembly movably connected to the proximal sub-assembly. The distal sub-assembly includes: a main body; an actuation member sleeved on the main body; and a plunger unit received in the main body; characterized in that the plunger unit is the unit described above.

It is preferred that the main body includes an arm which is releasably engaged with the plunger body to hold the plunger unit to the main body.

It is to be understood that both the foregoing general description and the following detailed description are exemplary and explanatory and are intended to provide a non-limiting explanation of the present invention as claimed.

BRIEF DESCRIPTION OF THE DRAWINGS

The accompanying drawings, which are included to provide a further understanding of the present invention and which constitute a portion of the specification, illustrate embodiments of the present invention and together with the description serve to explain the principle of the present invention. In the drawings.

DETAILED DESCRIPTION

In the present invention, the term "proximal part/end" refers to the part/end of the medicament delivery device, or the parts/ends of the members thereof, which is/are located closest to the medicament delivery site of a patient. Correspondingly, the term "distal part/end" refers to the part/end of the medicament delivery device, or the parts/ends of the members thereof, which is/are located farthest away from the medicament delivery site of the patient.

Figure 2:
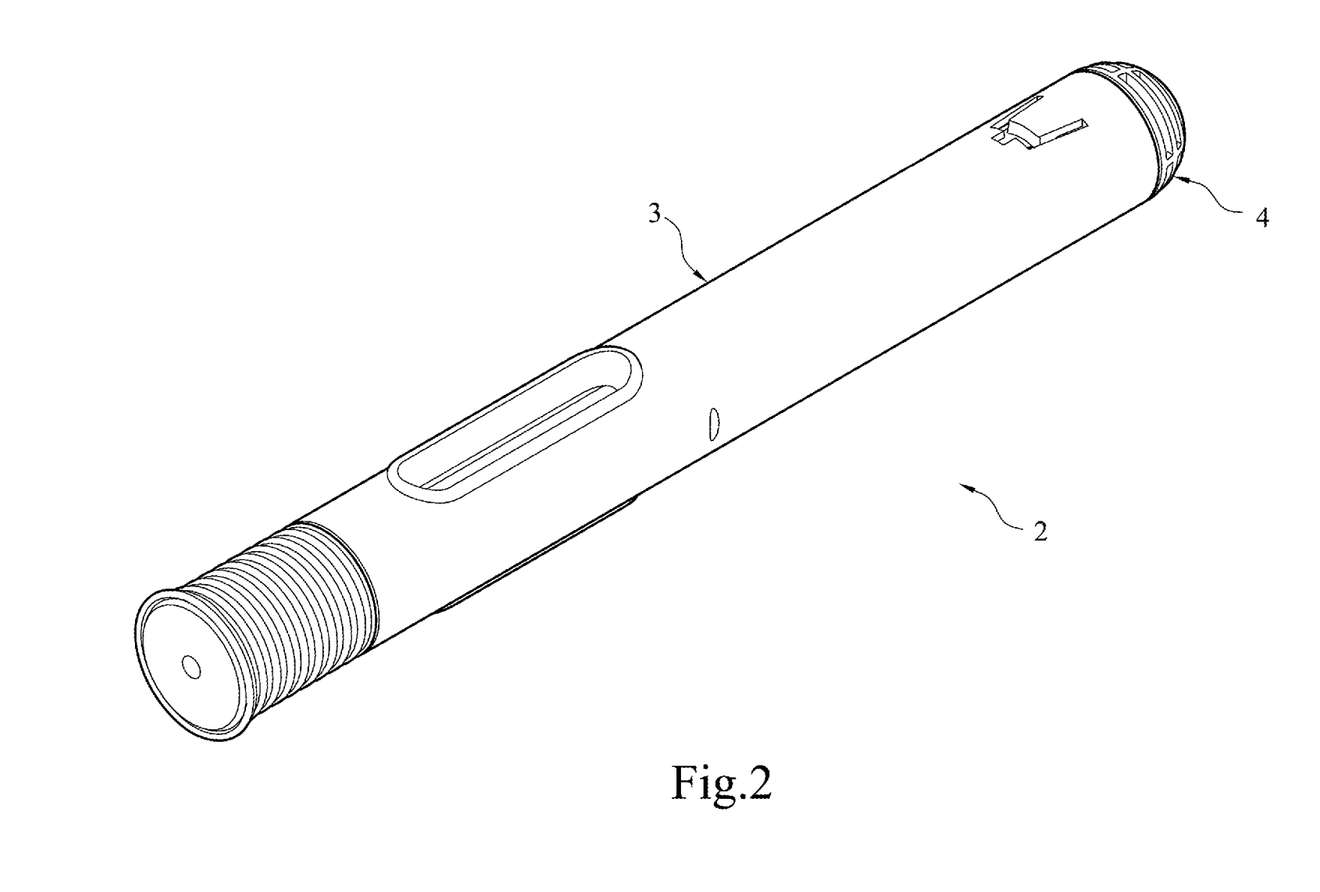
FIG. 2 is an assembled perspective view illustrating a medicament delivery device according to this invention.
Figure 3:
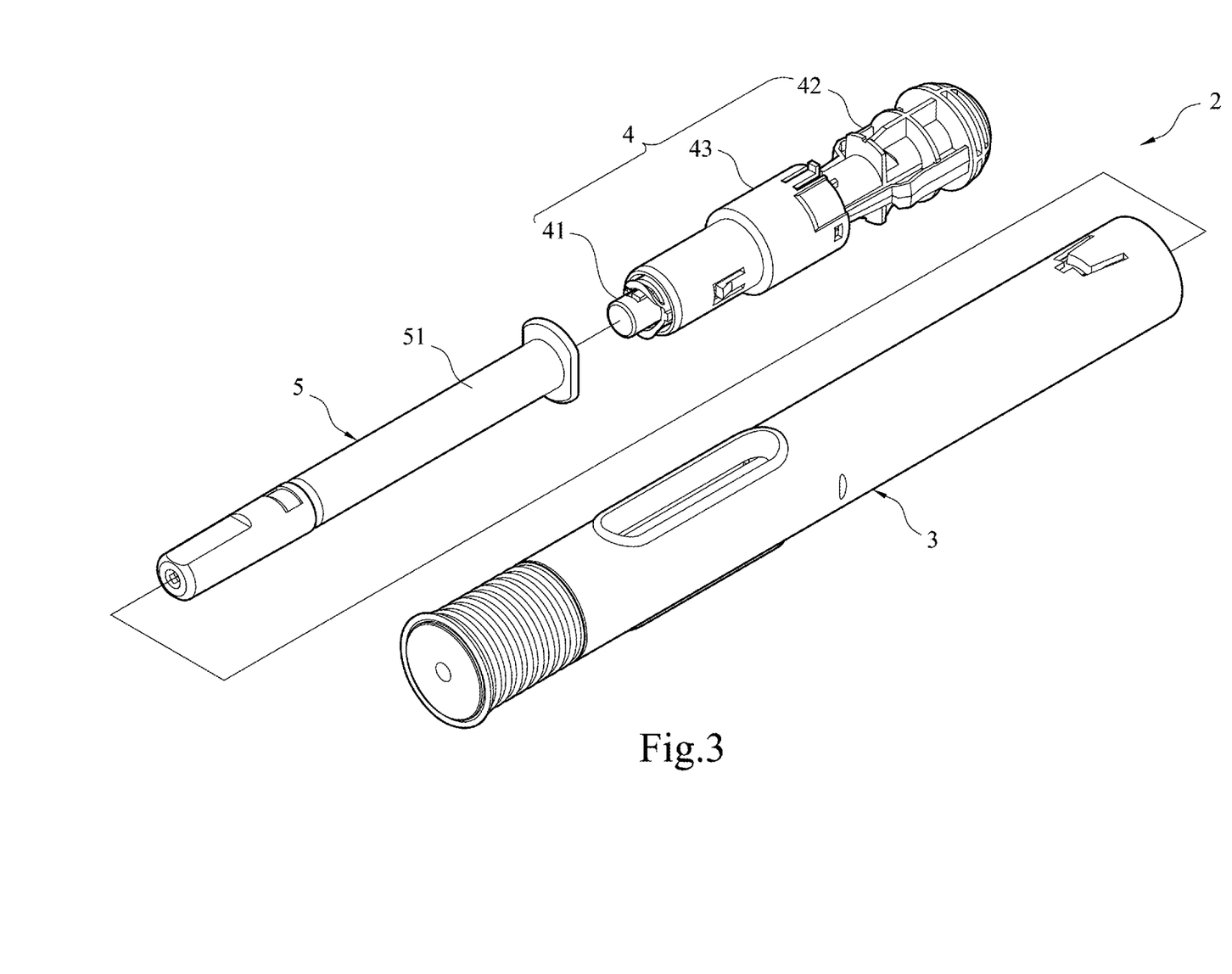
FIG. 3 is an exploded perspective view illustrating the medicament delivery device according to this invention.

As shown in FIGS. 2 and 3, a medicament delivery device 2 comprises a proximal sub-assembly 3, a distal sub-assembly 4 and an intermediate sub-assembly 5 which is arranged between the proximal sub-assembly 3 and the distal sub-assembly 4. Compared to the WO 2011-123024A1, the present invention will focus on the distal sub-assembly 4. Hence, the structure of the present invention which is the same as, or similar to, that disclosed in the WO 2011-123024A1 may be omitted from this specification.

Figure 4:
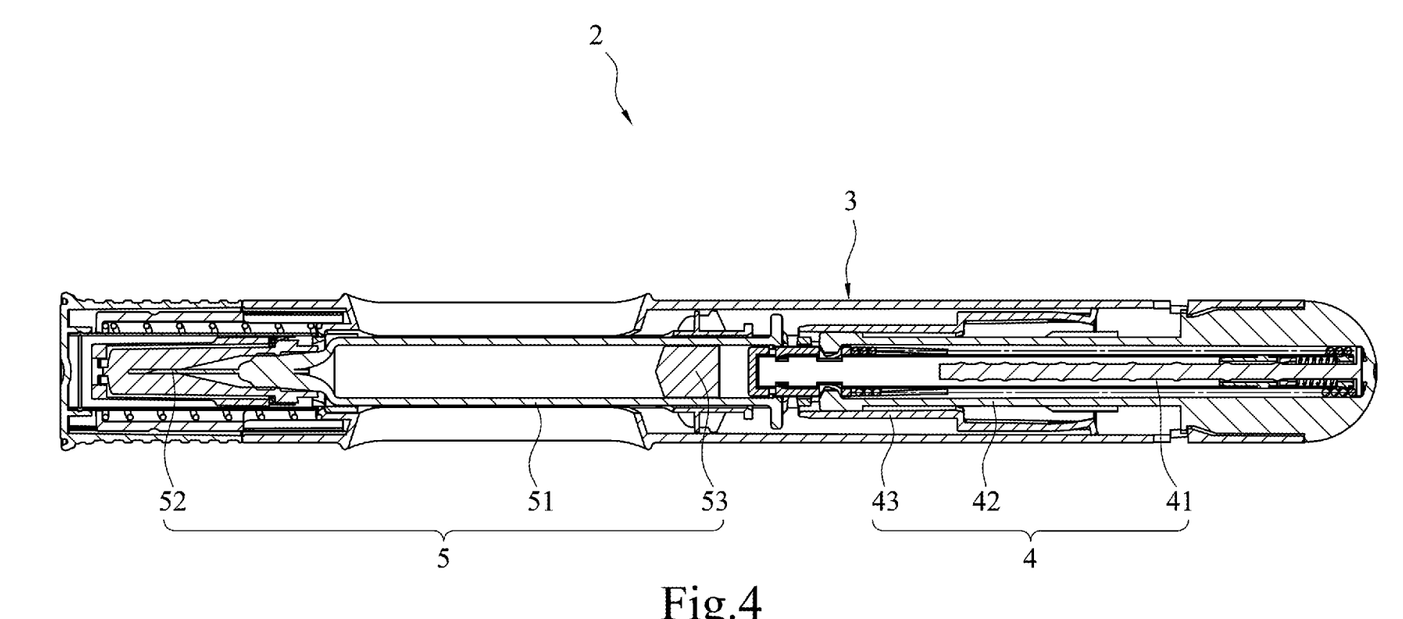
FIG. 4 is an assembled cross-sectional view illustrating the medicament delivery device of FIG. 2.

As shown in FIGS. 3 and 4, the intermediate sub-assembly 5 may include a container 51, a cannula 52 connected to a proximal end of the container 51, and a stopper 53 which is slidably received in the container 51. The distal sub-assembly 4 may include a main body 42, a plunger unit 41 slidably received in the main body 42, and an actuation member 43 sleeved on the main body 42.

Figure 5:
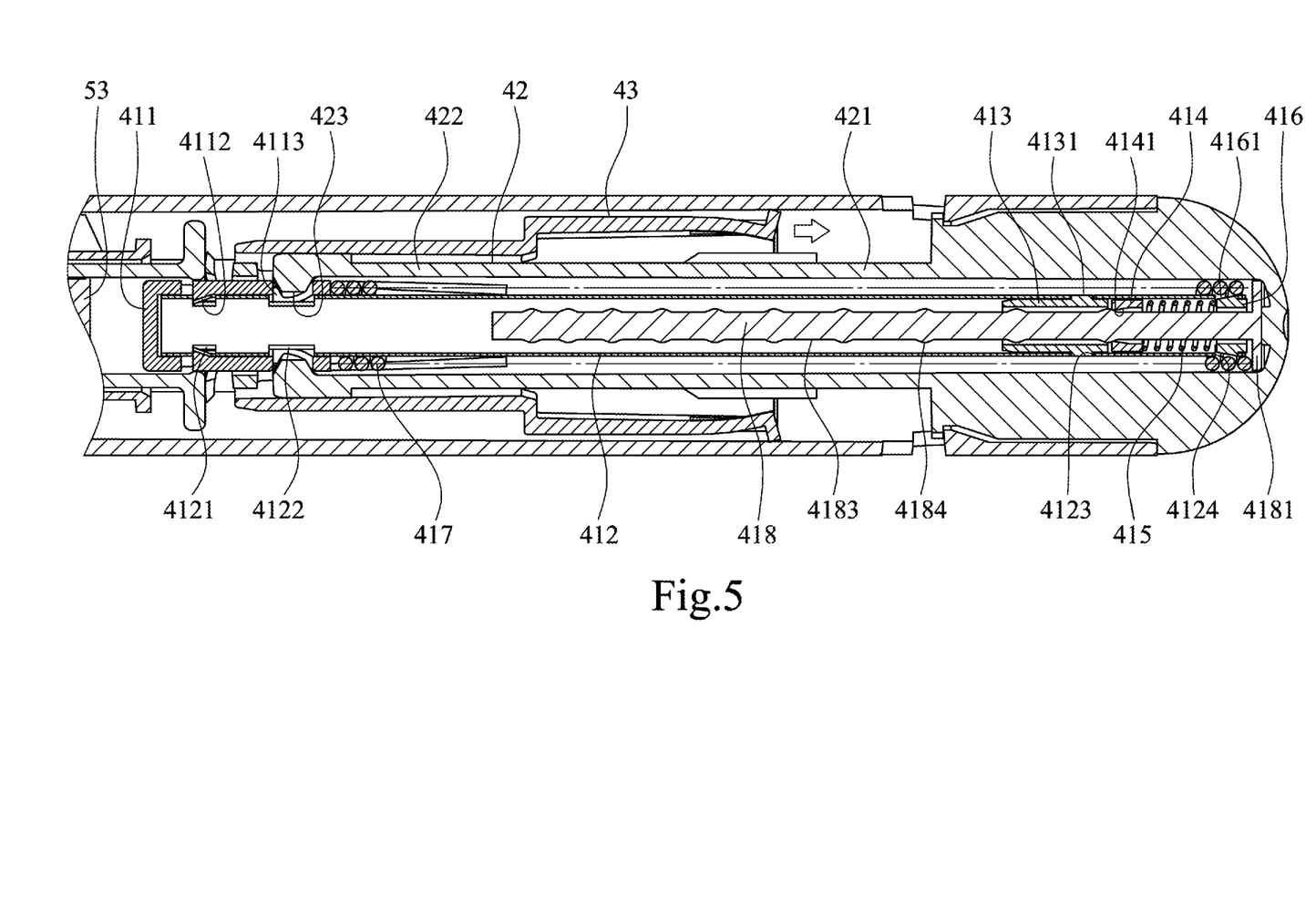
FIG. 5 is a partial cross-sectional view which enlarges the distal half of FIG. 4 and shows the medicament delivery device in a state before being used.

As shown in FIG. 5, the main body 42 may include a hollow cylinder 421 and a flexible arm 422, which constitutes a portion of the cylinder 421, with an inward barb 423 at the free end of the arm 422.

Figure 6:
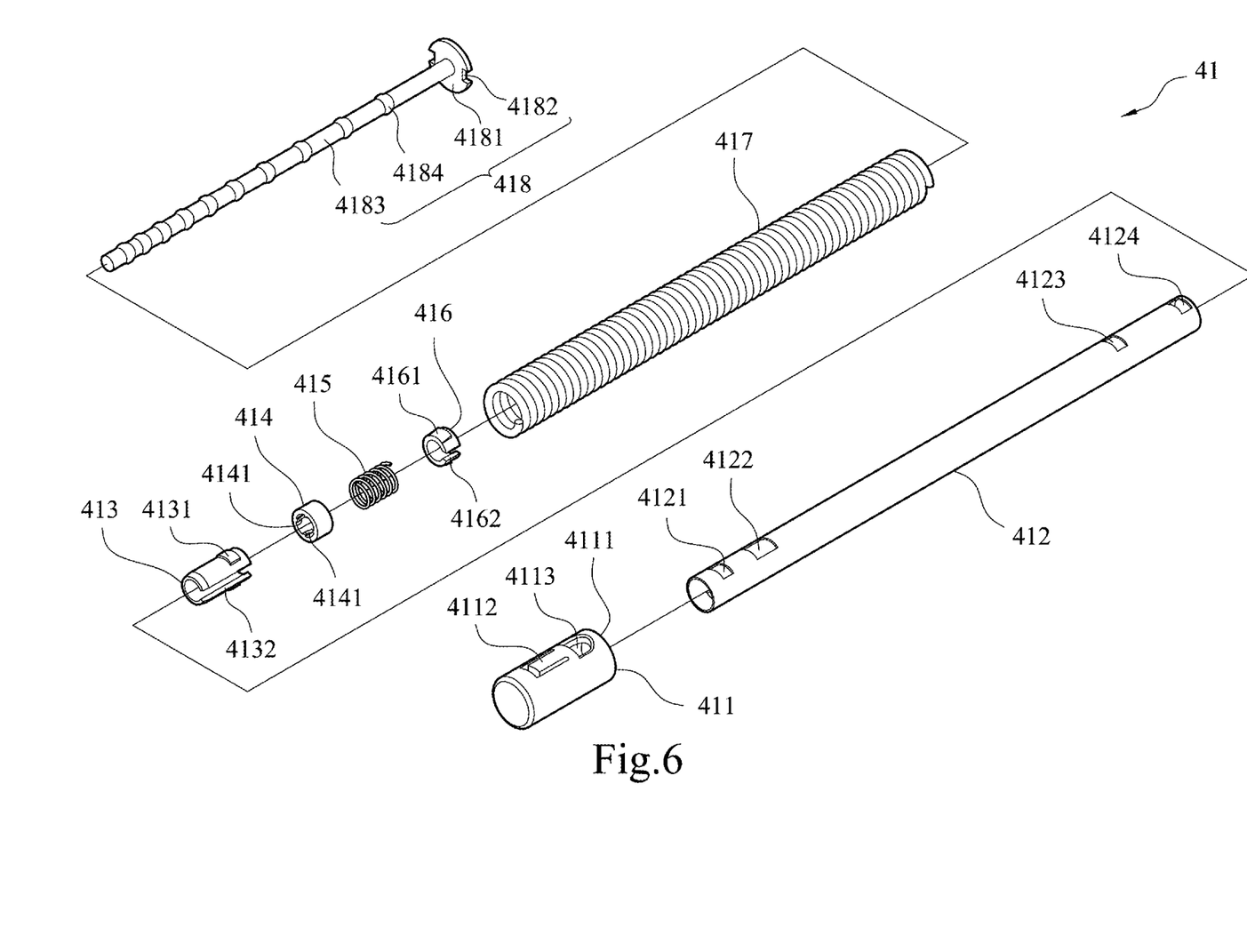
FIG. 6 is an exploded perspective view illustrating a plunger unit of the medicament delivery device of FIG. 2.

As shown in FIG. 6, the plunger unit 41 may include a hollow plunger head 411, a slender plunger sleeve 412, a c-shaped plug 413, a ring-shaped striker 414, a second biasing member 415, a c-shaped blocker 416, a first biasing member 417 and a rod member 418.

As shown in FIGS. 5 and 6, the plunger head 411 is formed with a closed end at the proximal end thereof, an open end 4111 at the distal end thereof, a cylindrical wall between the closed end and the open end 4111, two flexible tabs 4112 which constitute a portion of the wall and respectively have inward barbs at the free ends of the tabs 4112, and two holes 4113 respectively between the tabs 4112 and the open end 4111.

The plunger sleeve 412 has, on its cylindrical wall in sequence, with two first orifices 4121 and two second orifices 4122 near the proximal end thereof and two third orifices 4123 and two fourth orifices 4124 near the distal end thereof.

The plug 413 is formed with two outward protrusions 4131 on a cylindrical wall thereof, and a slit 4132 longitudinally extending along the entire length of the wall to make the plug 413 have a c-shaped cross section.

The striker 414 is formed with at least one wedge-shaped inward rib 4141 on an inner surface thereof. The thickness of the wedge-shaped rib 4141 gradually decreases in a direction from the proximal end to the distal end of the striker 414. In this embodiment, the striker 414 has four ribs 4141. Preferably, the ribs 4141 are symmetrically arranged around the inner surface of the striker 414.

The blocker 416 is formed with two outward ledges 4161 on cylindrical wall thereof, and a gap 4162 longitudinally extending along the entire length of the wall to make the blocker 416 have a c-shaped cross section.

The rod member 418 is formed with a disc-shaped rod head 4181, two notches 4182 on the rod head 4181, a rod body 4183 extending proximally from the center of the rod head 4181, and a plurality of ring-shaped bumps 4184 are formed along the length of the rod body 4183, and are equidistantly spaced from each other.

Assembly of the Plunger Unit

Firstly, as shown in FIGS. 5 and 6, the proximal end of the plunger sleeve 412 is inserted into the plunger head 411 through the open end 4111 of the plunger head 411 to the extent that the barbs of the tabs 4112 of the plunger head 411 snap into the first orifices 4121 of the plunger sleeve 412 and the holes 4113 of the plunger head 411 are aligned with the second orifices 4122 of the plunger sleeve 412. Secondly, the plug 413 is put into the plunger sleeve 412 through the distal end thereof. The C-shaped cross section of the plug 413 renders the plug 413 flexibility such that the plug 413 can be pressed into the plunger sleeve 412 and then expand to make the protrusions 4131 of the plug 413 be received in the third orifices 4123. Next, the striker 414 and the second biasing member 415 are, in order, inserted into the plunger sleeve 412 through the distal end thereof. Outer diameters of the striker 414 and the second biasing member 415 are smaller than inner diameter of the plunger sleeve 412 so that the striker 414 and second biasing member 415 are slidable within the plunger sleeve 412. Subsequently, the blocker 416 is set to the distal end of the plunger sleeve 412. The blocker 416 is similar to the plug 413, i.e. the blocker 416 has a flexible C-shaped cross section to allow the blocker 416 to be pressed into the plunger sleeve 412 and then expand and make the ledges 4161 of the blocker 416 be received in the fourth orifices 4124.

Furthermore, the first biasing member 417 is sleeved on the plunger sleeve 412 such that the proximal end of the first biasing member 417 contacts the distal end of the plunger head 411. Finally, the rod member 418 is inserted into the plunger sleeve 412 through central bores of the blocker 416, second biasing member 415, striker 414 and plug 413 until the rod head 4181 of the rod member 418 contacts the distal end of the first biasing member 417 to complete the assembling of the plunger unit 41.

The plunger unit 41 is then inserted into the main body 42 to the extent that the notches 4182 of the rod member 418 are engaged with bulges (not shown) inside the main body 42 and the barbs 423 of the arms 422 of the main body 42 snap into the holes 4113 of the plunger head 411 so as to hold the plunger unit 411 to the main body 42 and maintain the first biasing member 417 in a compressed state.

Alternatively, the rod member 418 is first inserted into the main body 42, followed by the first resilient member 417 and then the spring guide rod assembly (411, 412, 413, 414, 415 and 416). In addition, the rod member 418 can be first coupled with the main body 42 to form the first sub-unit. The first resilient member 417 is coupled with the spring guide rod assembly (411, 412, 413, 414, 415 and 416) to form the second sub-unit. Finally, the first sub-assembly is coupled to the second sub-assembly to complete the assembling.

Operation of the Plunger Unit

Figure 7:
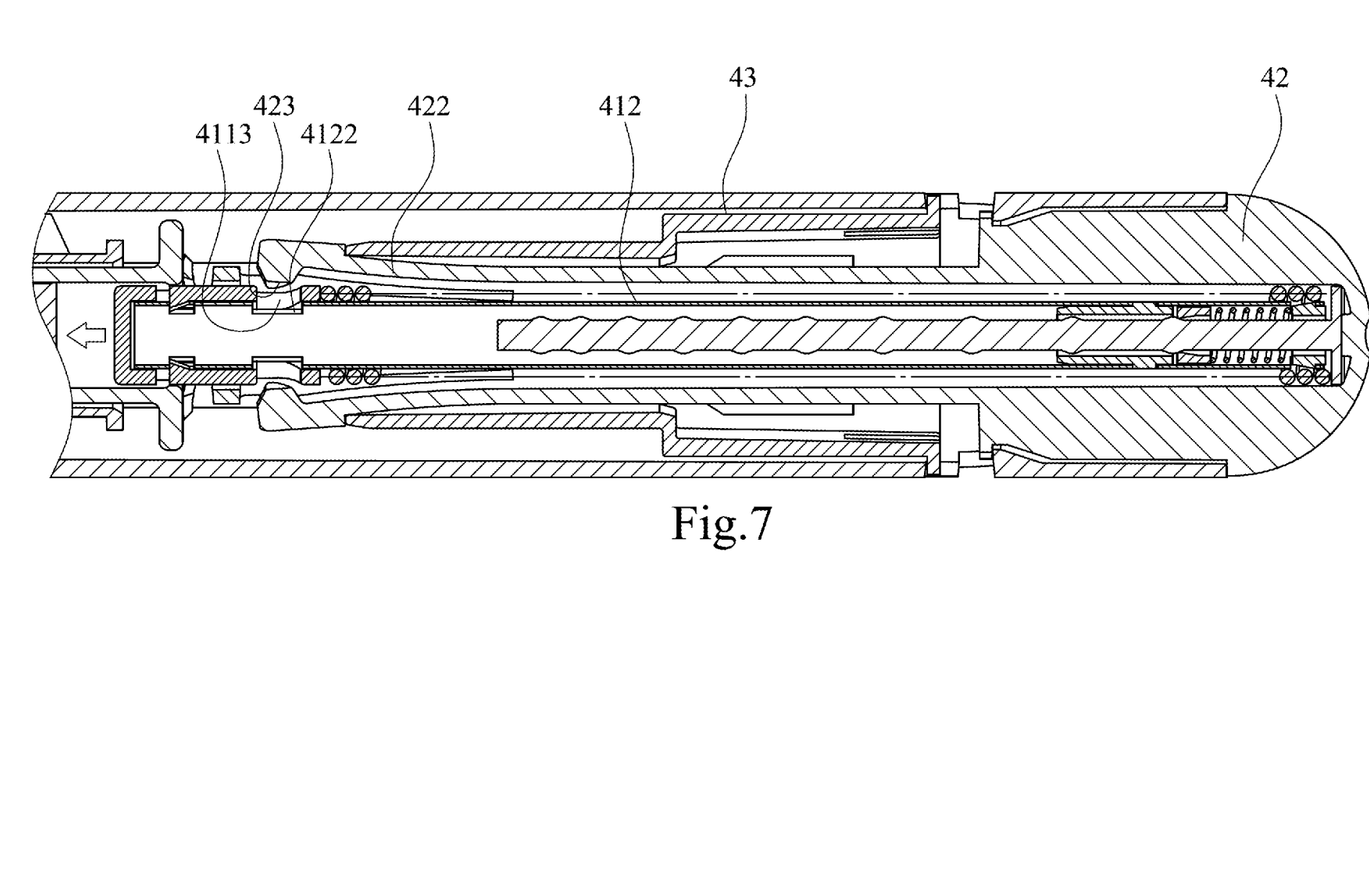
FIG. 7 is a partial cross-sectional view similar to FIG. 5 but shows that a plunger unit is released from an actuation member after the medicament delivery device is activated.

FIGS. 4 and 5 show the medicament delivery device in a state before being used. As shown in FIGS. 4 and 7, when a user presses a portion of the proximal sub-assembly 3 against his skin, the proximal sub-assembly 3 pushes the actuation member 43 to move in the distal direction so as to release the barbs 423 of the arms 422 of the main body 42 from the holes 4113 of the plunger head 411.

Figure 8:
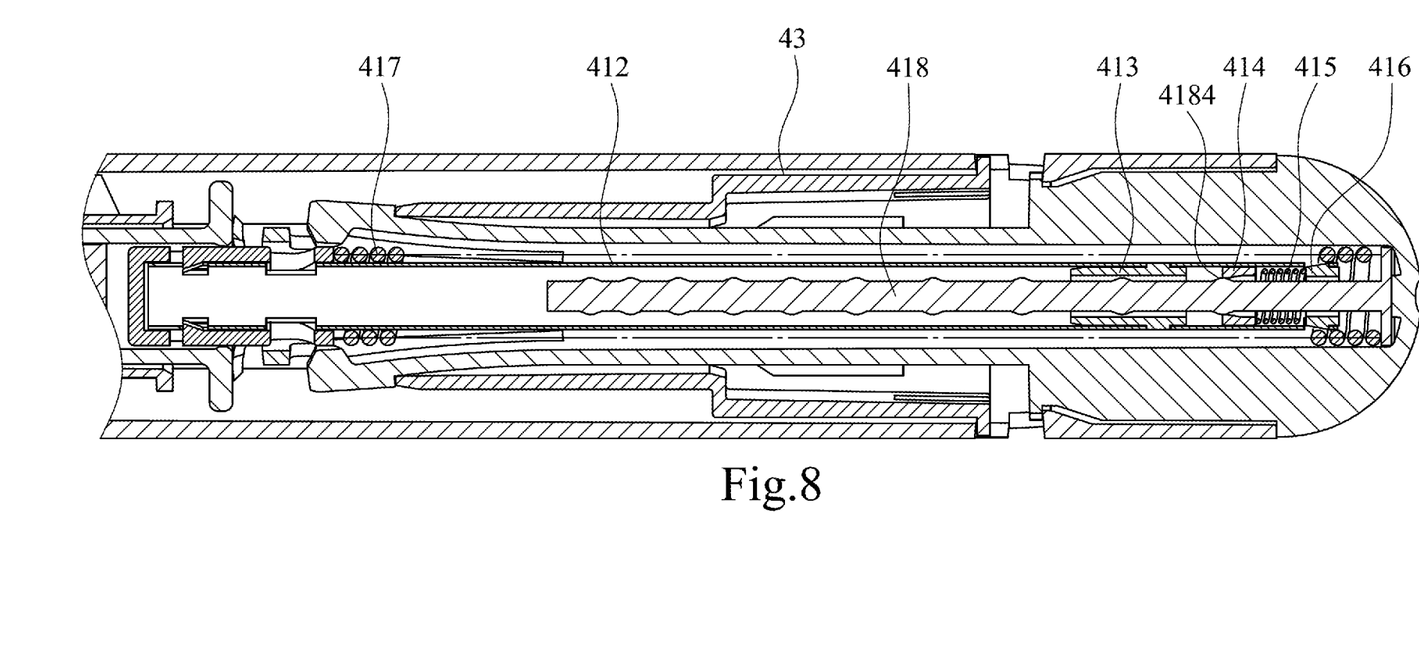
FIG. 8 is a partial cross-sectional view similar to FIG. 7 but shows that a striker is obstructed by a bump of a rod member.

As shown in FIGS. 4 and 8, the recovery force of the first biasing member 417, on one hand, pushes the rod head 4181 of the rod member 418 in the distal direction and against the main body 42 and, on the other hand, pushes the plunger head 411 together the plunger sleeve 412, plug 413 and blocker 416 to move in the proximal direction. The plunger head 411 may push the stopper 53 of the intermediate sub-assembly 5 to deliver the medicament within the container 51 though the cannula 52. In the meantime, the blocker 416 also pushes the second biasing member 415 and the striker 414 sliding in the proximal direction. However, the striker 414 and the second biasing member 415 will be temporarily obstructed by one of the bumps 4184 because the radius of each ring-shaped bump 4184 is almost equal to the distance from the center of the striker 414 to the portion with the largest thickness of the rib 4141.

Figure 9:
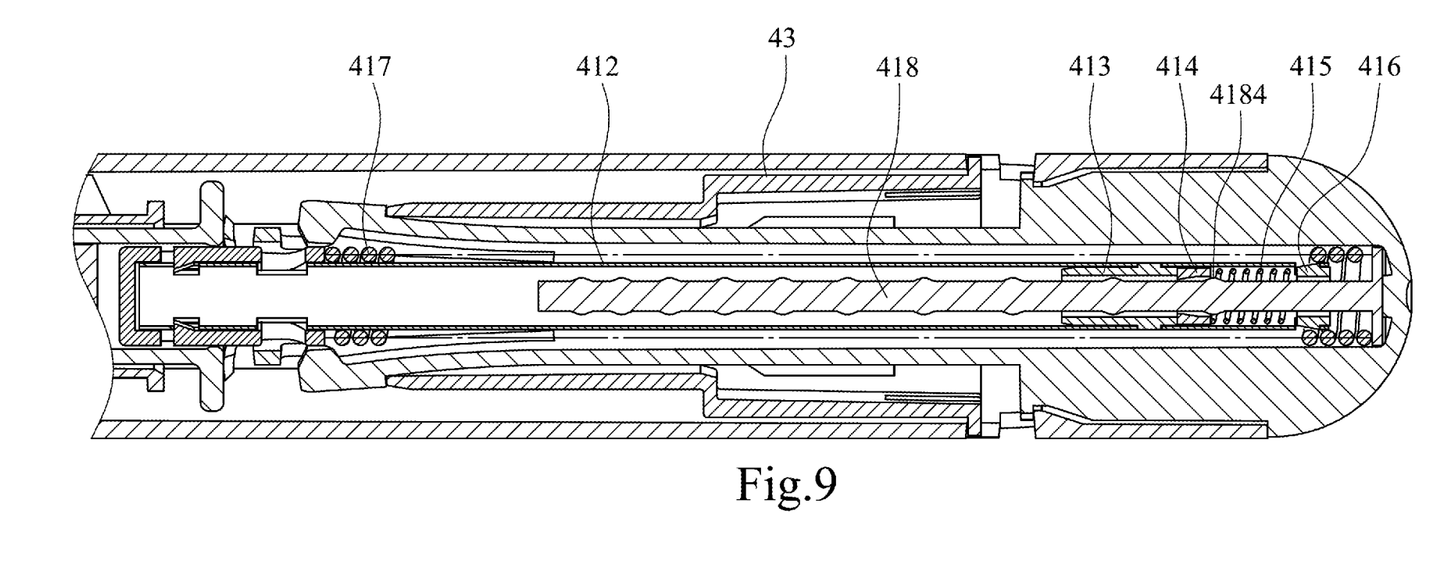
FIG. 9 is a partial cross-sectional view similar to FIG. 8 but shows that a striker slides over the bump and impacts a plug.

As shown in FIGS. 4 and 9, due to the striker 414 and the rod member 418 being made of material, such as plastic, with a little bit of resilience, the striker 414, which is obstructed by the bump 4184, will eventually be forced to slide over the bump 4184 of the rod member 418 when the blocker 416 together with the plunger sleeve 412 are consecutively moved in the proximal direction by the first biasing member 417.

Owing to the rib 4141 being wedge-shaped, when the portion of the rib 4141 with the greatest thickness slides over the bump 4184 of the rod member 418, the recovery force of the second biasing member 415 will push the striker 414 to quickly move in the proximal direction. Then, the striker 414 will impact the distal end of the plug 413 or next bump 4184 of the rod member 418 to create an audio signal or vibration (tactile feedback) for the user during the process of injection.

OTHER EMBODIMENTS

In a preferred embodiment, the plunger head 411 and plunger sleeve 412 may be integrally formed as a single member called a "plunger body".

In another preferred embodiment, the plunger head 411, plunger sleeve 412 and plug 413 may be integrally formed as a single member called a "plunger body".

In another preferred embodiment, after the striker 414 and the second biasing member 415 are put into the plunger sleeve 412 (or the plunger body in another preferred embodiment), the distal end of the plunger sleeve 412 may be bent inwards by a process to confine the second biasing member 415 within the plunger sleeve 412. In this embodiment, the blocker 416 may be omitted.

In further preferred embodiment, the striker 414 may be formed with a C-shape to make the striker 414 flexible and facilitate the striker 414 sliding over the bump 4184 of the rod member 418.

In another preferred embodiment, the striker 414 has no rib 4141. However, the cross section of the inner surface of the striker 414 may be in the shape of a wedge. In other words, the inner diameter of the striker 414 may gradually increase in the direction from the proximal end to the distal end.

In another preferred embodiment, the second biasing member 415 may be an integral part of the striker 414. The striker 414 comprises a resilient structure (not shown) integral therewith. The resilient structure accelerates the movement of the striker 414 after the striker 414 slides over the bump 4184 of the rod member 418, the audio signals (or tactile feedback) are created by the impact of the striker 414 on the next bump 4184 of the rod member 418.

In another preferred embodiment, the distances of two adjacent bumps 4184 of the rod member 418 may be equal or different through the whole rod body 4183 depending on the user's need of time intervals of audio signals (or tactile feedbacks).

Although afore-mentioned embodiments have been described with three sub-assemblies, the medicament delivery device 2 may be alternatively performed with two sub-assemblies. Specifically, the intermediate sub-assembly 5 may be incorporated with the proximal sub-assembly 3 so that the medicament delivery device 2 may merely comprise two sub-assemblies (i.e. a proximal sub-assembly 3 and a distal sub-assembly 4).

This invention has been disclosed in terms of specific embodiments. It will be apparent that many modifications can be made to the disclosed structures without departing from the present invention. Therefore, it is the intent of the appended claims to cover all such variations and modifications that are within the scope of this invention.

The invention claimed is:
1. A plunger unit comprising:
   a rod member;
   a plunger body movably mounted relative to the rod member;
   a first biasing member including two ends which respectively urges the plunger body and the rod member; and
   a striker that is movably mounted between the plunger body and the rod member, wherein the striker impacts the plunger body or the rod member to create signals when the first biasing member activates a movement of the plunger body relative to the rod member.

2. The plunger unit according to claim 1, wherein the plunger unit further comprises a second biasing member urging the striker and the plunger body.

3. The plunger unit according to claim 2, wherein the second biasing member is an integral part of the striker.

4. The plunger unit according to claim 2, wherein the plunger unit further comprises a blocker connected to the plunger body and the second biasing member urging the striker and the blocker.

5. The plunger unit according to claim 1, wherein the striker and the second biasing member are movably received in the plunger body and the first biasing member is sleeved outside the plunger body.

6. The plunger unit according to claim 5, wherein the plunger body includes a plunger head, a plunger sleeve connected to the plunger head and a plug received in the plunger sleeve,
wherein the striker and the second biasing member are received in the plunger sleeve and the first biasing member is sleeved outside the plunger sleeve, and
wherein the rod member passes through the second biasing member and the striker.

7. The plunger unit according to claim 5, wherein the rod member includes a rod body and a plurality of bumps on the rod body,
wherein the rod body passes through the second biasing member and the striker, and
wherein the bumps interfere with the striker when the striker is moved along the rod body.

8. The plunger unit according to claim 7, wherein the striker is in a C-shape or has a wedge-shaped rib.

9. The plunger unit according to claim 7, wherein the striker is ring-shaped or has a wedge-shaped rib.

10. The plunger unit according to the claim 7, wherein the rod member further includes a rod head from which the rod body extends, and
wherein the first biasing member urges the rod head and the plunger body.

11. The plunger unit according to claim 6, wherein the rod member includes a rod head, a rod body extending from the rod head, and a plurality of bumps on the rod body, and
wherein the first biasing member urges the rod head and the plunger head.

12. A medicament delivery device comprising:
a proximal sub-assembly; and
a distal sub-assembly movably connected to the proximal sub-assembly and including:
a main body;
an actuation member sleeved on the main body; and
a plunger unit received in the main body, where the plunger unit comprises:
a rod member;
a plunger body movably mounted relative to the rod member;
a first biasing member including two ends which respectively urges the plunger body and the rod member; and
a striker that is movably mounted between the plunger body and the rod member,
wherein the striker impacts the plunger body or the rod member to create signals when the first biasing member activates a movement of the plunger body relative to the rod member.

13. The medicament delivery device according to claim 12, wherein the main body includes an arm which is releasably engaged with the plunger body to hold the plunger unit to the main body.

14. A signaling assembly comprising:
a plunger sleeve;
a plunger head axially and rotationally fixed to a proximal end of the plunger sleeve;
a striker slidably positioned inside a distal end of the plunger sleeve between a plug and a blocker;
a rod member slidably positioned inside the plunger sleeve and the striker such that the rod member can move axially relative to both the striker and the plunger sleeve; and
a first biasing element having a distal end and a proximal end, where the proximal end abuts the plunger head and distal end abuts a rod head located on the rod member.

15. The signaling assembly of claim 14 where the rod member further comprises a plurality of bumps longitudinally spaced along the rod member.

16. The signaling assembly of claim 15 further comprising a second biasing element abutting the striker.

17. The signaling assembly of claim 16 where the striker further comprises an interior portion that narrows from a proximal end to a distal end, where the interior portion engages one or more of the plurality bumps when the plunger sleeve moves proximally.

18. The signaling assembly of claim 17 where the second biasing member exerts a force on the striker in the proximal direction when the rod member moves distally causing the striker to impact the plug or another one of the plurality of bumps during an injection of medicament resulting in a tactile or audible notification.

19. The signaling assembly of claim 17 where the interior portion comprises a plurality of ribs that are wedged shape and project radially inward.

20. The signaling assembly of claim 15 where the plurality of bumps are separated by a distance that is directly related to predetermined time interval of notification.

* * * * *